United States Patent [19]

Mullah et al.

[11] Patent Number: 5,736,626
[45] Date of Patent: Apr. 7, 1998

[54] SOLID SUPPORT REAGENTS FOR THE DIRECT SYNTHESIS OF 3'-LABELED POLYNUCLEOTIDES

[75] Inventors: Khairuzzaman Bashar Mullah, Union City; William A. Andrus, San Francisco, both of Calif.

[73] Assignee: The Perkin-Elmer Corporation, Foster City, Calif.

[21] Appl. No.: 593,031

[22] Filed: Jan. 29, 1996

[51] Int. Cl.$^6$ .................................................. C07H 21/00
[52] U.S. Cl. .............................. 536/25.3; 435/6; 435/810; 436/501; 536/22.1; 536/23.1; 536/24.1; 536/24.3; 536/24.31; 536/24.32; 536/24.33; 935/77; 935/78
[58] Field of Search .................... 435/6, 810; 436/501; 536/22.1, 23.1, 24.1, 24.3–24.33, 25.3; 935/77.78

[56] References Cited

U.S. PATENT DOCUMENTS

| | | | |
|---|---|---|---|
| 5,141,813 | 8/1992 | Nelson | 428/402 |
| 5,231,191 | 7/1993 | Woo et al. | 549/220 |
| 5,401,837 | 3/1995 | Nelosn | 536/25.32 |

OTHER PUBLICATIONS

Lee et al. Nucleic Acids Research, 21(16): 3761-3766 (1993) Allecic Discrimination by nick-translation PCR with fluorogenic probes.

Holland et al. Proc. Natl. Acad. Sci., 88: 7276–7280 Detection of specific polymerase chain by utilizing the 5'→3' exonuclease activity of the *Thermus aquaticus* DNA polymerase.

Livak et al. PCR Methods and Applications, 4:357-362, Cold Spring Harbor Laboratory Press, 1995 Oligonucleotides with Fluorescent Dyes at Opposite Ends Provide a Quenched Probe System Useful for Detection PCR Product and Nucleic Acid Hybridization.

Nelson et al. Nucleic Acids Research, 20(23): 6253-6259 (1992) Oligonucleotide labeling methods 3. Direct labeling of oligonucleotides employing a novel, non-nucleosidic, 2-aminobutyl-1, 3-propanediol backbone.

Gryaznov et al. Tetrahedron Letters, 34(8): 1261-1264 (1993) Anchor for One Step Release of 3'-Aminooligonucleotides from a Solid Support.

Peninsula Laboratories, Inc. Peninsula Laboratories, Inc. 1994-1995 Catalog, pp. 238-240, Belmont, California Chemical compound structure for: Rhodamine-CEP; DMT-5-Rhodamine-dU-CEP; DMT-Rhodamine-CPG.

Clontech Laboratories, Inc. Clontech 1994-1995 Catalog, Tools for the Molecular Biologist, pp. 113-124, Palo Alto, California Label-On Reagents; Aminomodifiers; Special Modification Reagents.

*Primary Examiner*—Ardin H. Marschel
*Attorney, Agent, or Firm*—Paul D. Grossman

[57] ABSTRACT

The compounds of the invention are exemplified by the class of diglycolate synthesis supports particularly useful as support reagents for the direct synthesis of 3'-labeled polynucleotides. Generally, the compounds of the invention have the structure

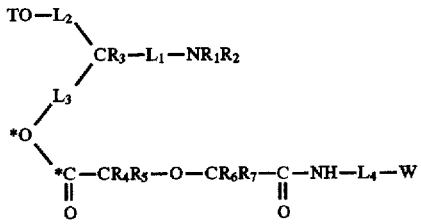

where T is an acid-cleavable hydroxyl protecting group, e.g., 4,4'-dimethoxytrityl; $L_1$ is a linker for connecting a 3'-terminal nitrogen to carbon; $L_2$ and $L_3$ are linkers for connecting oxygen and carbon; W is a solid support, e.g., CPG or polystyrene; $L_4$ is a linker for connecting the solid support to nitrogen; $R_1$ and $R_2$ are nitrogen substituents, e.g., hydrogen, lower alkyl, nitrogen protecting group, or label; and $R_3$ through $R_7$ are carbon substituents, e.g., hydrogen or lower alkyl. In a first particularly preferred embodiment, the synthesis supports of the invention are exemplified by compounds having the structure where DMT is 4,4'-dimethoxytrityl and W is polystyrene. In a second particularly preferred embodiment, the synthesis supports of the invention are exemplified by compounds having the structure where DMT and W are defined above.

16 Claims, 3 Drawing Sheets

$L_4$ = aminopropyl succinyl aminohexyl for CPG
$L_4$ = aminomethyl for polystyrene

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
 (A) LENGTH: 18 nucleotides
 (B) TYPE: nucleic acid
 (C) STRANDEDNESS: single
 (D) TOPOLOGY: linear (xi) SEQUENCE DESCRIPTION: SEQ ID NO: 1:

TCACAGTCTG ATCTCGAT 18

SOLID SUPPORT REAGENTS FOR THE DIRECT SYNTHESIS OF 3'-LABELED POLYNUCLEOTIDES

BACKGROUND

This invention relates generally to solid support reagents useful for the synthesis of functionalized polynucleotides. More particularly, the invention relates to synthesis supports useful for the direct synthesis of polynucleotides having a label located at the 3'-end and methods utilizing such reagents.

The continued rapid development of non-isotopically labeled polynucleotide probes, DNA/RNA amplification methods, automated DNA sequencing, and bioactive antisense and triplex synthetic reagents, has greatly increased the demand for chemically modified polynucleotides. One particularly useful polynucleotide modification is the introduction of a label at the 3'-end of the oligonucleotide.

Such 3'-labeling of synthetic polynucleotides can be most readily accomplished in one of two ways. In a first method, referred to herein as the "two-step labeling method", a primary aliphatic amine is introduced at the 3'-end of a polynucleotide, and subsequent to polynucleotide synthesis, the amino group is reacted with labels containing an electrophilic moiety, e.g., isothiocyanates or activated esters, e.g., NHS-esters. In a second alternative method, referred to herein as the "direct labeling method", a label is directly incorporated into the polynucleotide during or prior to synthesis.

The most effective and convenient method for introducing a label at the 3'-end of a synthetic polynucleotide is to use a direct labeling method utilizing an appropriately fuctionalized synthesis support because, (i) direct methods do not require a post-synthesis reaction step, thereby simplifying the synthesis of 3'-labeled polynucleotides; and (ii) direct methods avoid the problems associated with the low reaction yield (<60%) typically encountered when an amino-labeled oligonucleotide is reacted with a label, e.g., a dye-NHS-ester label, namely: (a) purification of the labeled oligonucleotide away from excess label; (b) purification of the labeled oligonucleotide away from unlabeled oligonucleotide; (c) increased costs associated with the low product yield caused by throwing away the large fraction of unlabeled oligonucleotides; and (d) irreversible capping of the 3'-amine functionality during synthesis.

However, a serious shortcoming of existing methods used for the direct 3'-labeling of polynucleotides is that reagents used for cleaving the oligonucleotide from the support also chemically degrades many types of labels, e.g., fluorescent dyes, e.g., rhodamine-based dyes, thereby radically altering their fluorescent properties. See P. E. Nelson et al., *Nucleic Acids Research* 20(23): 6253–6259 (1992), and U.S. Pat. Nos. 5,401,837 and 5,141,813, both patents being hereby incorporated by reference in their entirety. Thus, whenever rhodamine or other like dyes are used in current solid phase synthesis protocols, they must be attached using the less-desirable two-step method.

Therefore, it would be desirable to provide a synthesis support useful for the direct synthesis of 3'-labeled polynucleotides which does not require harsh cleavage conditions incompatible with base-labile labels.

SUMMARY

The present invention is directed towards our discovery of a diglycolate-based synthesis support useful for the direct synthesis of 3'-labeled polynucleotides.

It is an object of our invention to provide a synthesis support wherein cleavage of the polynucleotide product may be effected using mild conditions relative to ammonium hydroxide.

It is a further object of our invention to provide a synthesis support wherein cleavage of the polynucleotide product may be effected using conditions which are not destructive to rhodamine dyes.

It is another object of our invention to provide a synthesis support wherein direct synthesis of 3'-labeled polynucleotides may be performed using ammonium-hydroxide labile labels, e.g., tetramethyl rhodamine.

It is yet another object of our invention to provide a synthesis support wherein the cleavage reaction is significantly faster than that found using traditional synthesis supports.

It is another object of our invention to provide a synthesis support wherein the yield of 3'-labeled polynucleotide is substantially higher then that found using traditional supports.

In a first aspect, the foregoing and other objects of our invention are achieved by a synthesis support comprising a compound of the formula:

where T is an acid-cleavable hydroxyl protecting group, e.g., 4,4'-dimethoxytrityl; $L_1$ is a linker for connecting a 3'-terminal nitrogen to carbon; $L_2$ and $L_3$ are linkers for connecting oxygen and carbon; W is a solid support; $L_4$ is a linker for connecting the solid support to nitrogen; $R_1$ and $R_2$ are nitrogen substituents individually selected from the group consisting of hydrogen, lower alkyl, nitrogen protecting group, or label; and $R_3$ through $R_7$ are carbon substituents individually selected from the group consisting of hydrogen or lower alkyl.

In one preferred embodiment, W is CPG and $L_4$ has the structure

In an alternative preferred embodiment, W is non-swellable polystyrene and $L_4$ is methylene.

In yet another preferred embodiment, $L_4$ has the structure where n ranges from 0 to 10, and more preferably n=5.

In a first particularly preferred embodiment, the synthesis supports of the invention have the structure where DMT is 4,4'-dimethoxytrityl and W is polystyrene.

In a second particularly preferred embodiment, the synthesis supports of the invention have the structure where DMT is 4,4'-dimethoxytrityl and W is CPG.

In a third particularly preferred embodiment, the synthesis supports of the invention have the structure where DMT is 4,4'-dimethoxytrityl and W is polystyrene.

In a forth particularly preferred embodiment, the synthesis supports of the invention have the structure where DMT is 4,4'-dimethoxytrityl and W is CPG.

In a second aspect, the present invention includes methods for synthesizing a polynucleotide having a label or a nitrogen at the 3'-end utilizing conventional synthesis techniques in combination with the above-described synthesis supports. Specifically, the methods include the steps of (i) providing a synthesis support as described above; (ii) treating the synthesis support with acid to remove the acid-clearable hydroxyl protecting group; (iii) adding a protected nucleoside monomer and a weak acid, thereby forming a linkage; (iv) capping the unreacted sites on the solid support; (v) adding an oxidizing reagent; and (vi) repeating the above steps until polynucleotide-chain elongation is complete. After synthesis of the 3'-labeled polynucleotide, the product is then reacted from the solid support using a cleavage reagent and the polynucleotide is deprotected.

These and other objects, features, and advantages of the present invention will become better understood with reference to the following description, drawings, and appended claims.

DETAILED DESCRIPTION OF THE PREFERRED EMBODIMENTS

Reference will now be made in detail to the preferred embodiments of the invention, examples of which are illustrated in the accompanying drawings and formulas. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

The present invention is directed towards an improved diglycolate-based synthesis support useful for the synthesis of 3'-labeled polynucleotides. In particular, the synthesis supports of the invention have the following generalized structure,

FORMULA 1 where T is an acid-cleavable hydroxyl protecting group; $L_1$ is a linker for connecting a 3'-terminal nitrogen to carbon; $L_2$ and $L_3$ are linkers for connecting oxygen and carbon; W is a solid support; $L_4$ is a linker for connecting the solid support to nitrogen; $R_1$ and $R_2$ are nitrogen substituents individually including hydrogen, lower alkyl, nitrogen protecting group, or label; $R_3$ through $R_7$ are carbon substituents individually including hydrogen or lower alkyl; and W is a solid support.

The synthesis supports of the present invention provide several important advantages over current succinate-based synthesis supports used for the synthesis of polynucleotides. One particularly important advantage of the instant supports is that once synthesized, a 3'-labeled polynucleotide may be cleaved from the solid supports using relatively mild cleavage reagents, i.e., cleavage reagents which are weaker nucleophiles than ammonium hydroxide. Exemplary mild cleavage reagents include ethanolamine, methylamine/ammonium hydroxide mixtures, and mixtures of t-butylamine/water/methanol (1:2:1), e.g., see U.S. Pat. No. 5,231,191, hereby incorporated by reference in its entirety. This ability to use such mild cleavage reagents is practically important because it allows for the direct synthesis of 3'-labeled polynucleotides having labels which can not tolerate ammonium hydroxide, e.g., rhodamine dyes such as tetramethylrhodamine (TAMRA, sometimes abbreviated as "TMR"), e.g., 6-carboxytetramethylrhodamine.

A second significant advantage of the present invention is that, even while using mild cleavage reagents, the cleavage reaction is substantially faster than that observed using conventional methods and reagents, i.e., ammonium-hydroxide-based reagents in combination with succinate-based synthesis supports.

A third advantage of the supports of the instant invention is that high product yields may be obtained without manual intervention or harsh cleavage conditions. To achieve high yields using existing succinate-based synthesis supports, i.e., yields in the range of 99%, subsequent to synthesis, the polynucleotide-containing synthesis support is manually removed from the reaction cartridge, transferred to a glass vial, cleavage reagent is added, and the suspension is cooked at approximately 85° C. for several hours. An undesirable consequence of using this harsh cleavage protocol is that contaminants present in the solid support are extracted into the cleavage solution, thereby compromising the purity of the product oligonucleotide. In contrast to the cumbersome and harsh protocols required when using presently available supports, using the synthesis supports of the present invention, 99% yields may be obtained in a completely automated fashion without having to remove the synthesis support from the polynucleotide synthesizer or heat the cleavage reaction. Furthermore, because harsh cleavage conditions are not required, the product is not contaminated with material extracted from the solid support.

The terms "oligonucleotide" or "polynucleotide" as used herein refer to oligomers of natural or modified nucleoside or of non-nucleosidic analogs linked by phosphodiester bonds or analogs thereof ranging in size from a few monomeric units, e.g., 2–5, to several hundred monomeric units.

As used herein, the term "label" refers generally to any 3'-modifications of the polynucleotide including modifications which (i) facilitate detection, e.g., dyes, enzymes, spin-labels, or the like; (ii) facilitate capture of the polynucleotide to a solid substrate, e.g., biotin, haptens, and the like; (iii) affect solubility or modify cellular uptake, e.g., PEG, cholesteryl, triglycerides, and the like; and (iv) introduce moieties that participate in chemical reactions, e.g., psoralens, EDTA, phosphate, nucleic acid cleaving reagents, and the like.

In the present invention, W is a solid support on which the polynucleotide synthesis takes place. W can have a variety of forms and compositions, however, the solid support should be (i) substantially insoluble in polynucleotide synthesis reagents, (ii) chemically stable to polynucleotide synthesis reagents, (iii) capable of chemical derivitization, (iv) provide the desired oligonucleotide loading, (v) have adequate compression strength to withstand elevated pressure encountered during processing, and, (vi) available in a desirable particle size range and distribution. As used herein, the term "polynucleotide synthesis reagents" refers to solvents and reagents typically used in the polynucleotide synthesis process, e.g., iodine, methylene chloride, acetonitrile, tetrazole, n-methylimidazole, pyridine, acetic anhydride, lutidine, trifluroacetic acid, and the like.

In one preferred embodiment, W is an inorganic polymer. A wide variety of inorganic polymers can be employed in the present invention and these include, for example, silica, porous glass, aluminosilicates, borosilicates, metal oxides such as alumina and nickel oxide, various clays, and the like.

Preferably, the inorganic solid substrate is controlled pore glass (CPG). Controlled pore glass consists of uniformly milled and screened particles of almost pure silica that are honeycombed with pores of a controlled size. It is manufactured from a borosilicate material that has been specially heat treated to separate the borates from the silicates. The pores are formed by removing the borates by an acidic etching process, their size being dependent on the nature of the heating process. More preferably, the CPG is in the form of 150 μm diameter particles having 500 Å pores, e.g., *Users Manual Model 392 and 394 Polynucleotide Synthesizers*, pages 6–5 through 6–9, Applied Biosystems, Ver. 2.00, Doc. Rev. A, Part No. 902351 (1992), Applied Biosystems Division of The Perkin-Elmer Corporation, Foster City, Calif. (ABD).

Derivatization of CPG supports with amino-terminated linkers such as the $L_4$—NH moiety in the present invention is well known in the art of polynucleotide synthesis, e.g., Gait, Editor, *Oligonucleotide Synthesis*, pages 45–49 (IRL Press, 1984), and in fact, CPG beads derivatized with an alkyl amine having a primary amino loading of about 100 mmol/g are commercially available (Pierce Chemical Company, Rockford, Ill.). Briefly, in the case of alkyl amino substrates, the CPG is derivatized by reacting a suspension of CPG particles with an aminoalkyltrimethoxysilane reagent, filtered, and dried.

A second preferred solid substrate is non-swellable porous polystyrene, e.g., U.S. Pat. No. 5,047,524 which is incorporated herein by reference in its entirety. As used herein, "non-swellable" means that the porous polystyrene material remains substantially mechanically rigid, in particular, does not appreciably increase in volume, when exposed to polynucleotide synthesis reagents. As used herein, "porous" means that the non-swellable polystyrene contains pores having substantially uniform diameters in the range of between 100 and 4000 Å.

The polystyrene support is amino-derivatized by standard procedures, e.g., Wallace et at., pages 638–639 in Scouten ed., *Solid Phase Biochemistry* (John Wiley & Sons, 1980); Wright et at. *Tet. Let.*, 34:3373–3376 (1993); Bayer et at. U.S. Pat. No. 4,908,405, incorporated herein by reference; Applied Biosystems Research News, Model 390Z, February 1994. Briefly, in one preferred procedure, hydroxymethylpthalimide is reacted with the polystyrene support with a catalytic amount of methylsulfonic acid to form pthalimidomethyl polystyrene. This material is then treated with hydrazine to remove the pthalimide protecting group to give aminomethylated polystyrene. Typically, the amino loading varies from 10 to 60 μmoles of amino functionality per gram of nonswellable porous polystyrene. The loading level can be controlled by adjusting the concentrations of the reagents and reaction times.

A recently developed alternative polystyrene derivatizing chemistry replaces the terminal amino group with a free hydroxyl group by attaching several polyoxyethylene residues or chains having free hydroxyl groups available for coupling with the polynucleotide, e.g., Bayer and Rapp, U.S. Pat. No. 4,908,405; Gao et at., *Tetrahedron Lett.*, 32(40):5477–5480 (1991).

In a third preferred embodiment, W is a non-polystyrene organic polymer support. The polymer support can be derived from naturally occurring materials which are synthetically modified, and/or synthetic materials. Of particular interest are polysaccharides, particularly crosslinked polysaccharides, such as agarose, which is available as Sepharose™, dextran, which is available as Sephadex™, cellulose, starch, and the like. Other suitable materials include polyacrylamides, polyvinyl alcohols, silicones, Teflons™, and the like.

T refers generally to an acid-clearable hydroxyl protecting group. Preferably, T is the triphenylmethyl radical and its electron-donating-substituted derivatives, where, as used herein, the term "electron-donating" denotes the tendency of a substituent to release valence electrons to neighboring atoms in the molecule of which it is a part, i.e., it is electropositive with respect to neighboring atoms. Preferably, electron-donating substituents include amino, lower alkyl having between 1 and 8 carbon atoms, lower aryl having between 1 and 8 carbon atoms, alkoxy having from 1 to 8 carbon atoms, and the like. More preferably, the electron-donating substituents are methoxy. Exemplary trityls include 4,4'-dimethoxytdtyl (i.e. bis(p-anisyl) phenylmethyl), monomethoxytrityl, α-naphthyldiphenylmethyl, tri(p-methoxyphenyl)methyl, and the like. Attachment and cleavage conditions for these and other trityls can be found in Greene and Wuts, *Protective Groups in Organic Synthesis*, 2nd Edition (John Wiley, New York, 1991).

Linkers $L_1$, $L_2$, $L_3$, and $L_4$ are linking moieties which serve to link various elements of the compounds of the invention. Specifically, $L_1$ serves to link the 3'-terminal nitrogen of the synthetic polynucleotide to the polynucleotide itself, $L_2$ and $L_3$ serve to link carbon and oxygen, and $L_4$ serves to link the solid support to nitrogen. An additional purpose of linkers $L_1$ through $L_4$ is to provide appropriate spacing between the label, the solid support, and the oligonucleotide in order (i) to reduce the extent to which the label interferes with hybridization of the polynucleotide to a complementary target, (ii) to reduce the extent to which the label and/or solid support interferes with the synthesis of the polynucleotide, and (iii) to protect the integrity of the label during polynucleotide synthesis.

Preferably, linkers $L_1$ through $L_4$ are individually lower alkyl, lower alkylene oxide, amide, carbamate, sulfonamide, urea, succinate or other dicarboxylic acid derivatives, or any combination thereof, where, as used herein, alkylamide refers to moieties having the structure, where n ranges from 0 to 20, and dicarboxylic acid derivatives refers to moieties having the structure, where n ranges from 2 to 20. In a particularly preferred embodiment, n=2, i.e., the linker is succinate. As used herein, the term "lower alkyl" denotes straight-chain, branched-chain, and cyclized alkyl groups containing from 1 to 10 carbon atoms, and the term "lower alkylene oxide" denotes straight-chain, branched-chain, and cyclized alkylene oxide groups containing from 2 to 10 carbon atoms, e.g., polyethylene oxide. In a particularly preferred embodiment, $L_1$ is n-butyl or n-hexylamide; $L_2$ and $L_3$ are each methylene; and, when W is polystyrene, $L_4$ is methylene, and when W is CPG, $L_4$ is aminopropylsuccinylhexylamine.

In addition to the above-described preferred linking moieties, in a particularly preferred embodiment, linker $L_3$ is a moiety having an internal cleavage site which when cleaved provides an additional site for labeling an oligonucleotide once it has been cleaved from the support. An exemplary moiety useful for this purpose is a moiety containing a disulfide bond which when cleaved with dithiothreitol (DTT) forms an —SH moiety. A particularly preferred $L_3$ moiety has the structure Substituents $R_3$–$R_7$ are carbon substituents. Preferably $R_3$–$R_7$ are separately lower alkyl or hydrogen. More preferably, $R_3$–$R_7$ are hydrogen.

$R_1$ and $R_2$ are nitrogen substituents which can vary greatly depending on the nature of the desired final product. It will be appreciated that because $R_1$ and $R_2$ are not central features of the invention and provide a generic function, $R_1$ can have a wide variety of forms. $R_1$ and $R_2$ are chosen so that the bonded nitrogen atom is chemically stable during synthesis and subsequent oligonucleotide cleavage. Moreover, $R_1$ and $R_2$ are themselves stable to standard polynucleotide synthesis reagents.

If a reactive amino group is desired subsequent to polynucleotide clearage, $R_1$ and $R_2$ should not substantially interfere with the nitrogen reactivity. In this case, one of $R_1$ and $R_2$ is preferably lower alkyl, hydrogen, or a nitrogen protecting group, e.g., FMOC, tBOC, or other like nitrogen protecting groups. Most preferably, one of $R_1$ and $R_2$ is hydrogen.

In the case where either or both of $R_1$ or $R_2$ are labels introduced prior to polynucleotide synthesis as part of a direct labeling method, the label should be stable in the presence of DNA synthesis reagents and mild cleavage reagents. Such labels include fluorophores, enzymes, biotin, intercalators, cross-linkers, nucleic acid cleaving reagents, modifiers of cellular uptake, and the like. Preferably, the label is a rhodamine dye, e.g., tetramethylrhodamine.

Detailed descriptions of the chemistry used to form polynucleotides are provided elsewhere, e.g., Caruthers et al., U.S. Pat. No. 4,458,066; Caruthers et al., U.S. Pat. No. 4,415,732; Caruthers et al., *Genetic Engineering*, 4: 1–17 (1982); Users Manual Model 392 and 394 Polynucleotide Synthesizers, pages 6-1 through 6-22, Applied Biosystems, Part No. 901237 (1991). Accordingly, each of these references are hereby incorporated by reference in their entirety.

The phosphoramidite method of polynucleotide synthesis is the preferred method because of its efficient and rapid coupling and the stability of the starting materials. The synthesis is performed with the growing polynucleotide chain attached to a solid support, so that excess reagents, which are in the liquid phase, can be easily removed by filtration, thereby eliminating the need for purification steps between cycles.

The following briefly describes the steps of a typical polynucleotide synthesis cycle using the phosphoramidite method. First, the solid support is treated with acid, e.g., trichloroacetic acid, to remove the hydroxyl protecting group T, freeing the hydroxyl for a subsequent coupling reaction. An activated intermediate is then formed by simultaneously adding the protected phosphoramidite nucleoside monomer and a weak acid, e.g., tetrazole, and the like, to the reaction. The weak acid protonates the nitrogen of the phosphoramidite forming a reactive intermediate. Nucleoside addition is complete within 30 s. Next, a capping step is performed which terminates any polynucleotide chains that did not undergo nucleoside addition. Capping is preferably done with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, e.g., trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases are removed by treating the polynucleotide solution in base at an elevated temperature, e.g., 55° C.

EXAMPLES

The invention will be further clarified by a consideration of the following examples, which are intended to be purely exemplary of the invention and not to in any way limit its scope.

EXAMPLE 1

Figure 1:
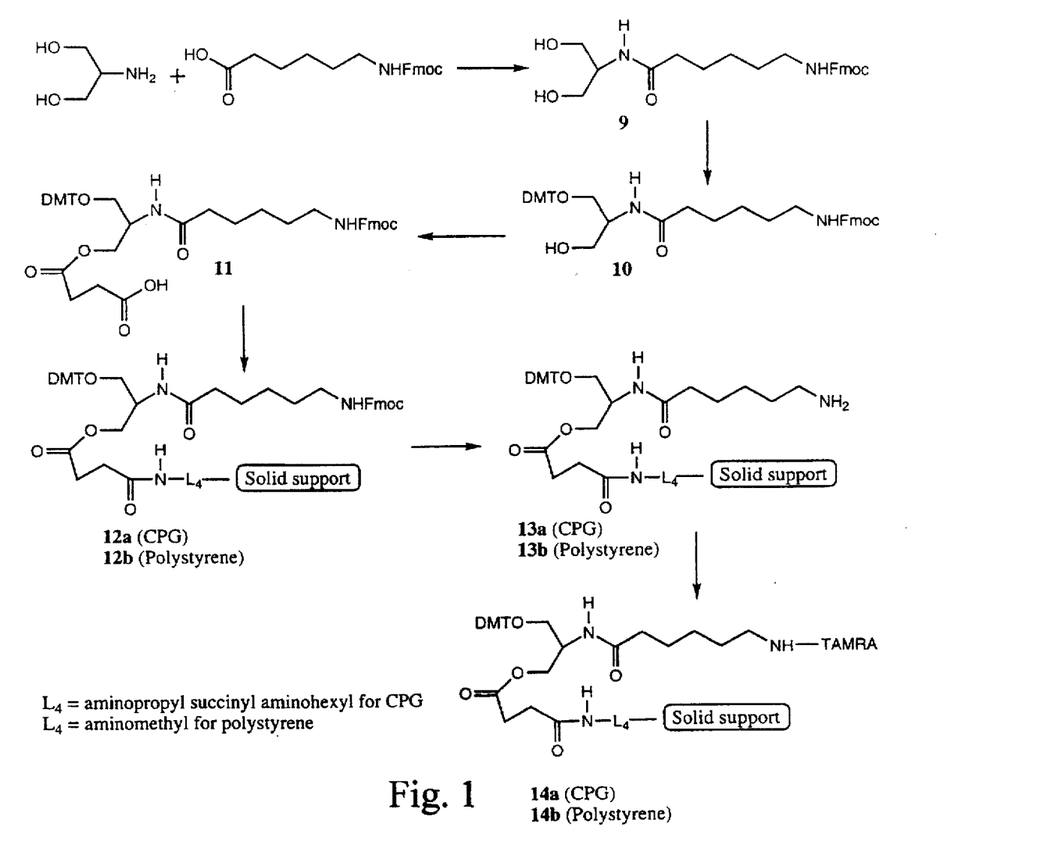
FIGS. 1, 2, and 3 schematically depict the synthesis of preferred synthesis supports of the present invention.

Synthesis of TAMRA Dye-Labeled CPG Support of Structure 14a (See FIG. 1)

Synthesis of Compound 9: Serinol (773 mg, 8.50 mmol), 1-hydroxybenzotriazol (574 mg, 4.25 mmol), (2-(1H-benzotdazol-1-yl)-1,1,3,3-tetramethyluronium hexafluorophosphate (1.61 g, 4.25 mmol), and diisopropylethylamine (1.68 g, 13 mmol) were added to a stirred solution of 6-N-Fmoc- aminocaproic acid in DMF (20 mL). The reaction mixture was stirred at room temperature under argon atmosphere for 2 h. DMF was removed by evaporation under reduced pressure. The residue was dissolved in $CHCl_3$ (100 mL) and washed with 5% aqueous HCl (1×50 mL), $H_2O$ (1×50 mL) and saturated brine (1×50 mL). The organic layer was dried ($MgSO_4$) and evaporated to give an oil which was dissolved in EtOH (10 mL) and refrigerated. Compound 9 crystallized as colorless fine needles (1.2 g, 66%). $^1H$ NMR ($CDCl_3$) d: 1.35 (m, 2H), 1.45 (m, 2H), 1.66 (m, 2H), 2.23 (t, J=7.2 Hz, 2H), 3.18 (m, 2H), 3.74 (dd, J=11.1, 4.2 Hz, 2H), 3.82 (dd, J=11.1, 3.9 Hz, 2H), 3.95 (m, 1H), 4.20 (t, J=6.6 Hz, 1H), 4.39 (d, J=6.6 Hz, 2H), 5.00 (bs, 1H), 6.40 (d, J=7.4 Hz, 1H), 7.28–7.43 (m, 4H), 7.58 (d, J=7.2 Hz, 2H), 7.76 (d, 1=7.2 Hz, 2H).

Synthesis of Compound 10: A solution of dimethoxytrityl chloride (1.16 g, 3.43 mmol) in dry pyridine (20 mL) was added dropwise to a stirred solution of compound 9 (1.33 g, 3.12 mmol) in pyridine (20 mL) at room temperature under nitrogen atmosphere. The addition was complete in 30 min. The flask was stoppered and stirred at room temperature for 48 h. TLC showed the presence of starting material and product 10. Pyridine was evaporated under reduced pressure and the residue was dissolved in $CHCl_3$ (50 mL) and washed with $H_2O$ (1×30 mL) and saturated brine (1×30 mL). The organic layer was dried ($MgSO_4$) and evaporated to give a yellowish oil. The product was isolated by column chromatography on silica gel eluting with 1% MeOH in $CHCl_3$. Appropriate fractions were combined and evaporated resulting in a colorless foam (1.31 g, 57%). $^1H$ NMR ($CDCl_3$) d: 1.26 (m, 2H), 1.45 (m, 2H), 1.62 (m, 2H), 2.16 (t, J=7.2 Hz, 2H), 2.85 (bs, 1H), 3.16 (m, 2H), 3.28 (dd, J=9.9, 4.8 Hz, 1H), 3.33 (dd, J=9.9 Hz, 4.5 Hz, 1H), 3.68 (m, 1H), 3.74 (s, 6H), 3.81 (m, 1H), 4.09 (m, 1H), 4.19 (t, J=6.6 Hz, 1H), 4.39 (d, J=6.6 Hz, 2H), 4.91 (bs, 1H), 5.95 (d, J=7.8 Hz, 1H), 6.82 (d, J=8.7 Hz, 4H), 7.20–7.42 (m, 13H), 7.58 (d, J=7.2 Hz, 2H), 7.75 (d, J=7.2 Hz, 2H).

Synthesis of Succinate 11: Succinic anhydride (82 mg, 0.82 mmol), $Et_3N$ (69 mg, 0.68 mmol) and 4-dimethylaminopyridine (42 mg, 0.34 mmol) were added to a solution of compound 10 (500 mg, 0.68 mmol) in $CH_2Cl_2$ (15 mL). The reaction mixture was stirred at room temperature for 3 h. The reaction mixture was diluted with $CH_2Cl_2$ (30 mL) and washed with 5% aqueous citric acid (1×30 mL) and saturated brine (2×30 mL). The organic layer was dried ($MgSO_4$) and evaporated to give a foam. The product was purified by column chromatography on silica gel eluting with a $CHCl_3$—MeOH gradient (0–5% MeOH). Appropriate fractions were combined and evaporated to give compound 11 as a colorless foam (439 mg, 78%). $^1H$ NMR ($CDCl_3$) d: 1.25 (m, 2H), 1.45 (m, 2H), 1.60 (m, 2H), 2.18 (t, J=7.5 Hz, 2H), 2.52 (s, 4H), 3.13 (m, 3H), 3.25 (dd, J=8.7, 4.0 Hz, 1H), 3.78 (s, 6H), 4.22 (m, 2H), 4.41 (m, 4H), 5.00 (unresolved t, 1H), 6.10 (d, J=7.2 Hz, 1H), 6.80 (d, J=8.5 Hz, 4H), 7.19–7.41 (m, 13H), 7.56 (d, J=7.5 Hz, 2H), 7.75 (d, J=7.2 Hz, 2H).

Synthesis of TAMRA Dye-Labeled CPG Support 14a: A mixture of CPG (500 Å, 40 µmol/g amine loading, 1 g, 40 µmol, (ABD)), compound 11 (67 mg, 80 µmol), 1-hydroxybenzotriazole (11 mg, 80 µmol), (2-(1H-benzotriazol-1-yl)-1,1,3,3-tetramethyluronium hexafluorophosphate (30 mg, 80 µmol), diisopropylethylamine (16 mg, 120 µmol) in DMF (8 mL) was shaken on a wrist-action shaker for 4 h at room temperature. The support was washed with DMF (3×10 mL), $CH_3CN$ (2×10 mL) and $CH_2Cl_2$ (1×10 mL) and dried under high vacuum overnight. A ninhydrin assay showed 6 µmol/g amine remained on the support. The support was capped with acetic anhydride/ lutidine in THF (10% solution, 5 mL) and 1-methylimidazol in THF (16% solution, 5 mL) for 2 h at room temperature.

Support 12a was washed with $CH_3CN$ (3×10 mL) and $CH_2Cl_2$ (1×10 mL) then treated with 20% piperidine in DMF (3×10 mL, 10 min each wash) to remove the Fmoc protecting group giving support 13a. The removal of the Fmoc group was monitored by measuring the UV absorbance of the solution at 302 nm. Support 13a was washed with DMF (3×10 mL), $CH_3CN$ (2×10 mL) and $CH_2C_{12}$ (1×10 mL) and dried under vacuum overnight. The support (500 mg, 16 µmol was then treated with TAMRA-NHS ester (ABD, p/n 400981) (26 mg, 49 µmol) and $Et_3N$ (10.1 mg, 100 µmol) in DMF (5 mL) for 42 h on a shaker to give dye-labeled support 14a. The support was washed with DMF (3×10 mL), $CH_3CN$ (2×10 mL) and $CH_2Cl_2$ (1×10 mL) and dried under high vacuum for 24 h. Ninhydrin assay showed 1 µmol/g amine left. The support was then capped with an acetic anhydride/lutidine mixture dissolved in THF (10% solution, 5 mL) and 1-methylimidazol in THF (16% solution, 5 mL) for 1 h and, washed with $CH_3CN$ (3×10 mL), $CH_2Cl_2$ (2×10 mL) and dried under high vacuum for 24 h. The trityl cation assay showed a final loading of 30.3 µmol/g.

EXAMPLE 2

Synthesis of TAMRA Dye-Labeled Polystyrene Support of Structure 14b (See FIG. 1)

High cross linked polystyrene (1000 Å, 10 µmol/g amine loading, 2 g, 20 µmol, (ABD)) was reacted with compound 11 from Example 1 (34 mg, 40 µmol), 1-hydroxybenzotriazole (5.5 mg, 40 µmol), (2-(1H-benzotriazol-1-yl)-1,1,3,3-tetramethyluronium hexafluorophosphate (15 mg, 40 µmol), and diisopropylethylamine (8 mg, 60 μmol) in DMF (10 mL) on a wrist-action shaker for 4 h at room temperature. The support was washed with DMF (3×10 mL), CH$_3$CN (2×10 mL) and CH$_2$Cl$_2$ (1×10 mL) and dried under high vacuum overnight. A ninhydrin assay showed 0.6 μmol/g amine left on the support. The support was capped with acetic anhydride/lutidine in THF (10% solution, 5 mL) and 1-methylimidazol in THF (16% solution, 5 mL) for 2 h at room temperature. Support 12b was washed with CH$_3$CN (3×10 mL) and CH$_2$C$_{12}$ (1×10 mL). Trityl cation assay gave 9 μmol/g loading of compound 11 on the polystyrene support. Support 12b was then treated with 20% piperidine in DMF (3×10 mL, 10 min each wash) to remove the Fmoc protecting group to give support 13b. The removal of the Fmoc group was monitored by measuring the UV absorbance of the solution at 302 nm. Support 13b was washed with DMF (3×10 mL), CH$_3$CN (2×10 mL) and CH$_2$Cl$_2$ (1×10 mL), and dried under vacuum overnight. The support (1 g, 9 umol) was then treated with TAMRA-NHS ester (15 mg, 28.5 μmol) and Et$_3$N (8.6 mg, 85 μmol) in DMF (10 mL) at room temperature for 36 h on a shaker to give support 14b. The support was washed with DMF (3×10 mL), CH$_3$CN (2×10 mL) and CH$_2$Cl$_2$(1×10 mL) and dried under high vacuum for 24 h. A ninhydrin assay indicated less than 0.5 μmol/g amine remaining. The support was then capped with acetic anhydride/lutidine in THF (10% solution, 5 mL) and 1-methylimidazol in THF (16% solution, 5 mL) for 1 h and then washed with CH$_3$CN (3×10 mL,), CH$_2$Cl$_2$(2×10 mL) and dried under high vacuum for 24 h. The trityl cation assay showed a final loading of 8.8 μmol/g.

EXAMPLE 3

Figure 2:
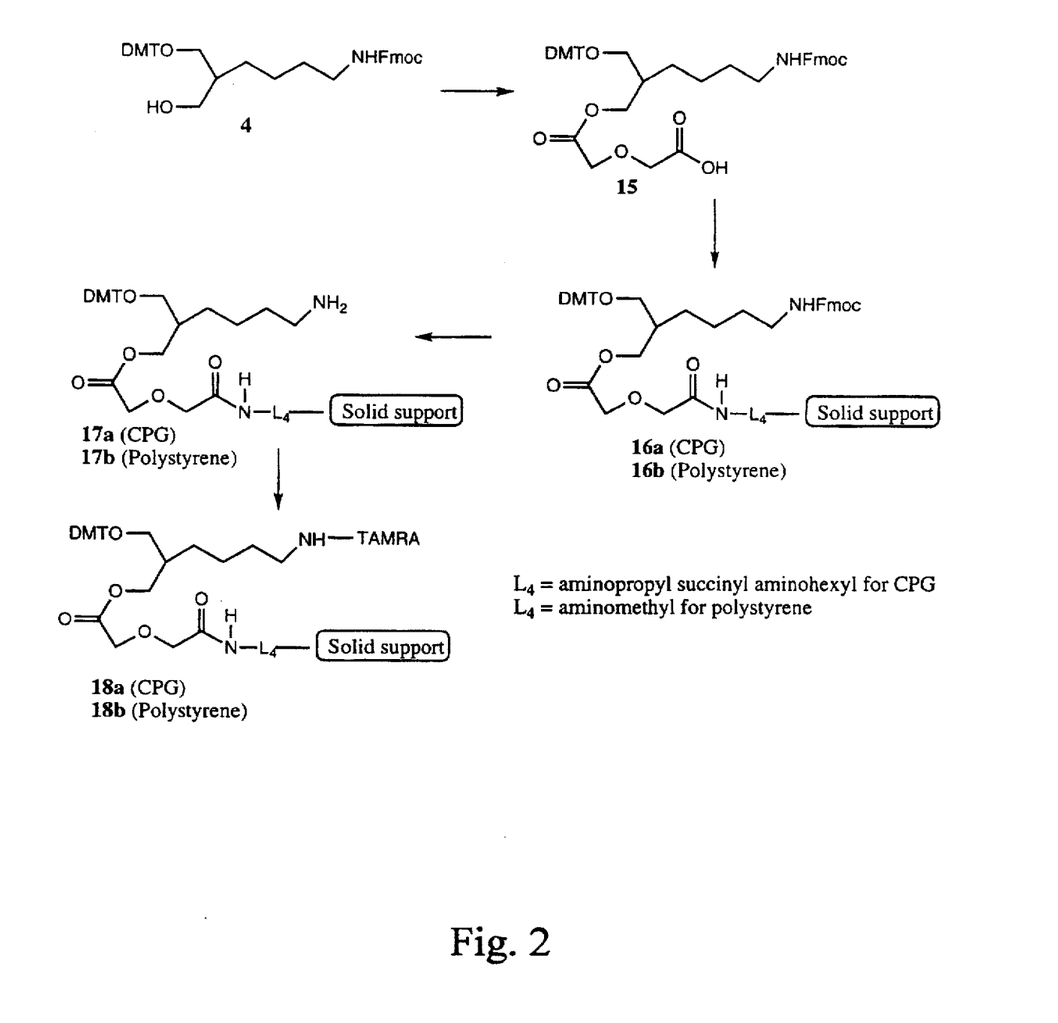

Synthesis of TAMRA Dye-Labeled CPG Support of Structure 18a (See FIG. 2)

Synthesis of 1-O-Dimethoxytrityl-2-(N-Fmoc-4-aminobutyl)-1,3-propanediol Compound 4: Compound 4 was synthesized following the procedure described by Nelson et al., *Nucleic Acids Research* 20: 6253–6259 (1992). A solution of dimethoxytrityl chloride (3.66 g, 10.82 mmol) in dry pyridine (60 mL) was added dropwise to a stirred solution of 2-(N-Fmoc-aminobutyl)-1,3-propanediol (4.0 g, 10.82 mmol) in pyridine (50 mL) at room temperature under nitrogen atmosphere. The addition was complete in 2 h. The flask was stoppered and stirred at room temperature for 48 h. TLC showed the presence of starting material and product 4. Pyridine was removed by evaporation under reduced pressure and the residue was dissolved in CHCl$_3$ (100 mL) and washed with H$_2$O (1×100 mL) and saturated brine (1×100 mL). The organic layer was dried (MgSO$_4$) and evaporated to give a yellowish oil. The product was isolated by column chromatography on silica gel eluting with 1% MeOH in CHCl$_3$. Appropriate fractions were combined and evaporated to a colorless foam (3.4 g, 46%). $^1$H NMR (CDCl$_3$) d: 1.15–1.45 (m, 6H), 1.88 (m, 1H), 2.44 (t, J=5.7 Hz, 1H), 3.07 (dd, J=9.3, 7.5 Hz, 1H), 3.12 (m, 2H), 3.29 (dd, J=9.3, 4.2 Hz, 1H), 3.64 (m, 2H), 3.78 (s, 6H), 4.20 (t, J=6.8 Hz, 1H), 4.39 (d, J=6.8 Hz, 2H), 4.72 (unresolved t, 1H), 6.82 (d, J=9.0 Hz, 4H), 7.25–7.43 (m, 13H), 7.58 (d, J=7.2 Hz, 2H), 7.75 (d, J=7.2 Hz, 2H).

Synthesis of Diglycolate 15: A solution of diglycolic anhydride (81 mg, 0.94 mmol in CH$_2$Cl$_2$ (5 mL) was added dropwise to a mixture of E$_3$N (90 mg, 0.89 mmol), 4-dimethylaminopyridine (45 mg, 0.37 mmol), and compound 4 (500 mg, 0.74 mmol) in CH$_2$Cl$_2$ (15 mL) at 0° C. (ice bath) under argon atmosphere. After the addition was complete (10 min), the ice bath was removed and the reaction mixture was stirred at room temperature for 1 h. The reaction mixture was diluted with CHCl$_3$ (30 mL) and washed with 5% aqueous citric acid (1×50 mL) and saturated brine (2×50 mL). The organic layer was dried (MgSO$_4$) and evaporated to give a foam. The product was purified by column chromatography on silica gel eluting with a CHCl$_3$—EtOH gradient (2–10% EtOH). Appropriate fractions were combined and evaporated to give compound 15 as a colorless foam (354 mg, 60%). $^1$H NMR (CDCl$_3$)d: 1.00–1.25 (m, 6H), 1.75 (m, 1H), 2.88 (m, 4H), 3.70 (s, 6H), 3.96 (s, 2H), 4.04 (s, 2H), 4.13 (m, 3H), 4.31 (d, J=6.9 Hz), 5.18 (bs, 1H), 6.74 (d, J=8.7 Hz, 4H), 7.18–7.34 (m, 13H), 7.53 (d, J=7.5 Hz, 2H), 7.67 (d, J=7.5 Hz, 2H).

Synthesis of TAMPA Dye Labeled CPG Support 18a: A mixture of CPG (500 Å, 40 μmol/g amine loading, 2 g, 80 gmol), compound 15 (126 mg, 160 μmol), 1-hydroxybenzotriazole (22 mg, 160 μmol), (2-(1H-bertzotriazol-1-yl)-1,1,3,3-tetramethyluronium hexafluorophosphate (61 mg, 160 μmol), and diisopropylethylamine (35 mg, 270 μmol) in DMF (10 mL) was shaken on a wrist-action shaker for 4 h at room temperature. The support was washed with DMF (3×10 mL), CH$_3$CN (2×10 mL) and CH$_2$Cl$_2$ (1×10 mL) and dried under high vacuum overnight. A ninhydrin assay showed 3 μmol/g amine left on the support. The trityl cation assay gave 37.5 μmol/g loading of compound 15 on the CPG support. The support was capped with acetic anhydride/lutidine in THF (10% solution, 5 mL) and 1-methylimidazol in THF (16% solution, 5 mL) for 2 h at room temperature. Support 16a was washed with CH$_3$CN (3×10 mL) and CH$_2$Cl$_2$(1×10 mL) then treated with 20% piperidine in DMF (3×10 mL, 10 min each wash) to remove the Fmoc protecting group giving support 17a containing a free amino group. The removal of the Fmoc group was monitored by measuring the UV absorbance of the solution at 302 nm. Support 17a was washed with DMF (3×10 mL), CH$_3$CN (2×10 mL) and CH$_2$Cl$_2$(1×10 mL), and dried under vacuum overnight. Support 17a (500 mg, 19 umol) was then treated with TAMRA-NHS ester (30 mg, 57 μmol) and Et$_3$N (13.1 mg, 130 μmol) in DMF (5 mL) for 42 h on a shaker to afford dye labeled support 18a. The support was washed with DMF (3×10 mL), CH$_3$CN (2×10 mL) and CH$_2$Cl$_2$(1× 10 mL) and dried under high vacuum for 24 h. A ninhydrin assay indicated 1 μmol/g amine was left on the support. The support was then capped with acetic anhydride/lutidine in THF (10% solution, 5 mL) and 1-methylimidazol in THF (16% solution, 5 mL) for 1 h and then washed with CH$_3$CN (3×10 mL), CH$_2$Cl$_2$ (2×10 mL) and dried under high vacuum for 24 h. The trityl cation assay showed a final loading of 36 μmol/g.

EXAMPLE 4

Synthesis of TAMRA Dye-Labeled Polystyrene Support of Structure 18b (See FIG. 2)

High cross linked polystyrene (1000 Å, 10 μmol/g amine loading, 2 g, 20 μmol), was treated with compound 15 (32 mg, μmol), 1-hydroxybenzotriazole (5.5 mg, 40 μmol), (2-(1H-benzotriazol-1-yl)-1,1,3,3-tetramethyluronium hexafluorophosphate (15 mg, 40 μmol), and diisopropylethylamine (8 mg, 60 μmol) in DMF (10 mL) on a wrist-action shaker for 4 h at room temperature. The support was washed with DMF (3×10 mL), CH$_3$CN (2×10 mL) and CH$_2$Cl$_2$ (1×10 mL) and dried under high vacuum overnight.

A ninhydrin assay showed 0.5 µmol/g amine left on the support. The support was capped with acetic anhydride/lutidine in THF (10% solution, 5 mL) and 1-methylimidazol in THF (16% solution, 5 mL) for 2 h at room temperature. Support 16b was washed with $CH_3CN$ (3×10 mL) and $CH_2Cl_2$ (1×10 mL). Trityl cation assay gave 9 µmol/g loading of compound 15 on the polystyrene support. Support 16b was treated with 20% piperidine in DMF (3×10 mL, 10 min each wash) to remove the Fmoc protecting group giving support 17b. Support 17b was washed with DMF (3×10 mL), $CH_3CN$ (2×10 mL) and $CH_2Cl_2$ (1×10 mL) and, dried under vacuum for overnight. Support 17b (1 g, 9 µmol) was treated with TAMRA-NHS ester (15 mg, 28.5 µmol) and $Et_3N$ (8.6 mg, 85 µmol) in DMF (10 mL) at room temperature for 36 h on a shaker to give support 18b. The support was washed with DMF (3×10 mL), $CH_3CN$ (2×10 mL) and $CH_2Cl_2$(1×10 mL) and dried under high vacuum for 24 h. A ninhydrin assay showed less than 0.5 µmol/g amine left. The support was capped with acetic anhydride/lutidine in THF (10% solution, 5 mL) and 1-methylimidazol in THF (16% solution, 5 mL) for 1 h and then washed with $CH_3CN$ (3×10 mL), $CH_2Cl_2$ (2×10 mL) and dried under high vacuum for 24 h. The trityl cation assay showed a final loading of 8.7 µmol/g.

EXAMPLE 5

Figure 3:
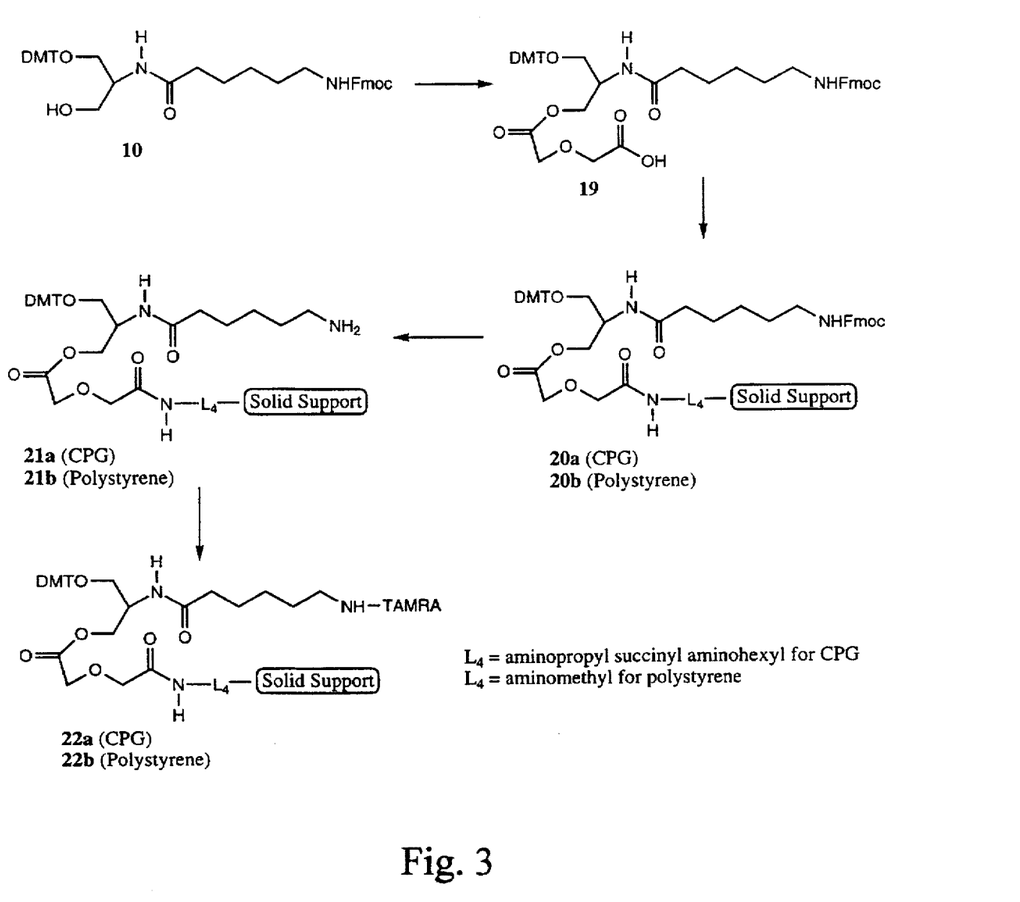

Synthesis of TAMRA Dye-Labeled CPG Support of Structure 22a (See FIG. 3)

Synthesis of Diglycolate 19: A solution of diglycolic anhydride (64 mg, 0.55 mmol) in $CH_2Cl_2$ (5 mL) was added to a mixture of $Et_3N$ (67 mg, 0.66 mmol), 4-dimethylaminopyridine (34 mg, 0.28 mmol) and compound 10 (400 mg, 0.55 mmol) in $CH_2Cl_2$ (15 mL) at 0° C. under argon atmosphere. After the addition was complete (10 min), the ice bath was removed and the reaction mixture was stirred at room temperature for 1 h. The reaction mixture was diluted with $CH_2Cl_2$ (30 mL) and washed with 5% aqueous citric acid (1×50 mL) and saturated brine (2×50 mL). The organic layer was dried ($MgSO_4$) and evaporated to give a foam. The product was purified by column chromatography on silica gel eluting with a $CHCl_3$-EtOH gradient (2–10% EtOH). Appropriate fractions were combined and evaporated to give compound 19 as a colorless foam (260 mg, 56%). $^1H$ NMR ($CDCl_3$) d: 1.20 (m, 2H), 1.39 (m, 2H, 1.58 (m, 2H), 2.18 (t, J=7.5 Hz, 2H), 2.90–3.25 (m, 4H), 3.80 (s, 6H), 3.86 (s, 4H), 4.00–4.40 (m, 6H), 4.85 (unresolved t, 1H), 5.92 (d, J=7.2 Hz, 1H), 6.75 (d, J=8.1 Hz, 4H), 7.20–7.40 (m, 13H), 7.52 (d, J=7.2 Hz, 2H), 7.69 (d, J=7.2 Hz, 2H).

Synthesis of TAMRA Dye Labeled CPG support 22a: A mixture of CPG (500 Å, 33 µmol/g amine loading, 1 g, 33 µmol), compound 19 (56 mg, 66 µmol), 1-hydroxybenzotriazole (9 mg, 66 µmol), (2-(1H-benzotriazol-1-yl)-1,1,3,3-tetramethyluronium hexafluorophosphate (25 mg, 66 µmol), and diisopropylethylamine (13 mg, 100 µmol) in DMF (6 mL) was shaken on a wrist-action shaker for 4 h at room temperature. The support was washed with DMF (3×8 mL), $CH_3CN$ (2×8 mL) and $CH_2CL_2$ (1×8 mL) and dried under high vacuum for overnight. A ninhydrin assay showed 3 µmol/g amine left on the support. The trityl cation assay gave 29 µmol/g loading of compound 19 on the CPG support. The support was capped with acetic anhydride/lutidine in THF (10% solution, 3 mL) and 1-methylimidazol in THF (16% solution, 3 mL) for 2 h at room temperature. Support 20a was washed with $CH_3CN$ (3×8 mL) and $CH_2CL_2$(1×8 mL) then treated with 20% piperidine in DMF (3×5 mL, 10 min each wash) to remove the Fmoc protecting group giving support 21a containing a free amino group. Support 21a was washed with DMF (3×8 mL), $CH_3CN$ (2×8 mL) and $CH_2CL_2$(1×8 mL), and dried under vacuum overnight. Support 21a (500 mg, 15 µmol) was then treated with TAMRA-NHS ester (24 mg, 45 µmol) and $Et_3N$ (11 mg, 110 µmol) in DMF (5 mL) for 42 h on a shaker resulting in dye labeled support 22a. Support 22a was washed with DMF (3×8 mL), $CH_3CN$ (2×8 mL) and $CH_2CL_2$ (1×8 mL) and dried under high vacuum for 24 h. A ninhydrin assay showed 1.2 µmol/g amine left on the support. The support was capped with acetic anhydride/lutidine in THF (10% solution, 3 mL) and 1-methylimidazol in THF (16% solution, 3 mL) for 1 h and then washed with $CH_3CN$ (3×8 µmL), $CH_2CL_2$ (2×8 mL) and dried under high vacuum for 24 h. The trityl cation assay showed a final loading of 28 µmol/g.

EXAMPLE 6

Synthesis of TAMRA Dye-Labeled Polystyrene Support of Structure 22b (See FIG. 3)

High cross linked polystyrene (1000 Å, 10 µmol/g amine loading, 1 g 10 µmol), was treated with compound 19 (17 mg, 20 µmol), 1-hydroxybenzotriazole (3 mg, 20 µmol), (2-(1H-benzotriazol-1-yl)-1,1,3,3-tetramethyluronium hexafluorophosphate (8 mg, 20 µmol), and diisopropylethylamine (8 mg, 60 µmol) in DMF (10 mL) on a wrist-action shaker for 4 h at room temperature to give 20b. The support was washed with DMF (3×10 mL), $CH_3CN$ (2×10 mL) and $CH_2Cl_2$ (1×10 mL) and dried under high vacuum overnight. A ninhydrin assay showed 0.5 µmol/g amine left on the support. The support was capped with acetic anhydride/lutidine in THF (10% solution, 5 mL) and 1-methylimidazol in THF (16% solution, 5 mL) for 2 h at room temperature. Support 20b was washed with $CH_3CN$ (3×10 mL) and $CH_2Cl_2$ (1×10 mL). Trityl cation assay gave 9.2 µmol/g loading of compound 19 on the polystyrene support. Support 20b was treated with 20% piperidine in DMF (3×10 mL, 10 min each wash) to remove the Fmoc protecting group to give support 21b. Support 21b was washed with DMF(3×10 mL), $CH_3CN$ (2×10 mL) and $CH_2Cl_2$ (1×10 mL) and, dried under vacuum overnight. Support 21b (1 g, 9.2 umol) was treated with TAMRA-NHS ester (15 mg, 28.5 µmol) and $Et_3N$ (8.6 mg, 85 µmol) in DMF (10 mL) at room temperature for 36 h on a shaker to give support 22b. The support was washed with DMF (3×10 mL), $CH_3CN$ (2×10 mL) and $CH_2Cl_2$ (1×10 mL) and dried under high vacuum for 24 h. A ninhydrin assay indicated less than 0.5 µmol/g amine left on the support. The support was capped with acetic anhydride/lutidine in THF (10% solution, 5 mL) and 1-methylimidazol in THF (16% solution, 5 mL) for 1 h and then washed with $CH_3CN$ (3×10 mL), $CH_2Cl_2$ (2×10 mL) and dried under high vacuum for 24 h. The trityl cation assay showed a final loading of 8.8 µmol/g.

EXAMPLE 7

Synthesis of Double Dye Labeled Oligonucleotides using the Supports of the Invention Doubled dye labeled oligonucleotides were synthesized using TAMRA-labeled supports 14a, 14b, 18a, 18b, and 22a, DNA FastPhosphoramidites and the fluorescent dye amidites FAM-, TET-, HEX- in 40–1000 nmol scale, where "FAM refers" to 6-carboxyfluorescein, "TET" refers to 6-carboxy-4,7,2',7'-tetrachlorofluorescein, and "HEX" refers to 6-carboxy-4,7,2',4',5',7'-hexachlorofluorescein. Automated oligonucleotide synthesis was performed on an Applied Biosystems Model 394 DNA/RNA synthesizer (ABD) according to the general procedures described in the operators manual.

The oligonucleotide sequence 5'>FAM-TCA CAG TCT GAT CTC GAT-TAMRA<3' was synthesized in 0.2 µmol scale by using TAMRA labeled supports 18a and 22a, DNA FastPhosphoramidites (User Bulletin number 85, 1994, Applied Biosystems Division) and FAM amidite (User Bulletin number 78, 1994, Applied Biosystems Division). The standard 0.2 µmol synthesis cycle was slightly modified by extending the coupling time of FAM-amidite by an additional 120 s (User Bulletin number 78, 1994, Applied Biosystems Division). After completion of the synthesis, oligonucleotides were autocleaved from the support by treating the support with a mixture of $MeOH:t-BuNH_2:H_2O$ (1:1:2), e.g., U.S. Pat. No. 5,231,191, such patent incorporated herein by reference in its entirety, using a 1 h autocleavage procedure ("END CE procedure") as described in the operators manual for the Applied Biosystems Model 394 DNA/RNA synthesizer. Base protecting groups were removed by heating the mixture at 85° C. for 1 h or at 65° C. for 3 h. More than 99% of oligonucleotides were cleaved from each of the supports.

The same oligonucleotide sequence mentioned above was also synthesized on the 394 DNA/RNA synthesizer in 40 nanomole scale using TAMRA labeled support 18b, DNA FastPhosphoramidites (User Bulletin number 85, 1994, Applied Biosystems Division) and FAM amidite (User Bulletin number 78, 1994, Applied Biosystems Division). Similarly the standard 40 nanomol synthesis cycle was slightly modified by extending coupling time of FAM by additional 120 sec (User Bulletin number 78, 1994, Applied Biosystems Division). More than 99% of oligonucleotides were cleaved from each of the supports.

TAMRA labeled supports 14a and 14b were also used for the synthesis of the above mentioned oligonucleotide in 0.2 µmol scale as described above. The oligonucleotides were cleaved from the supports by 2 h autocleavage protocol (END RNA) as described in operators manual for the 394 DNA/RNA using $MeOH:tBuNH_2:H_2O$ (1:1:2). More than 92% of the oligonucleotide was cleaved from the support in 2 h. However the oligonucleotide could be cleaved from the support and base deprotected by treating the support bound oligonucleotide in 1 mL of $MeOH:t-BuNH_2:H_2O$ (1:1:2) at 85° C. for 1 h. More than 99% of oligonucleotides were cleaved from each of the supports. The solid support matrix, CPG or polystyrene, did not make any difference in the rate of cleavage of oligonucleotide from the support. The crude yield of the above mentioned oligonucleotides was 25–30 ODU at 0.2 µmol scale and 7–10 ODU at 40 nanomol scale. The crude oligonucleotides were analysed by both reverse phase and anion exchange HPLC.

The reverse phase HPLC system used to analyze the oligonucleotide products was as follows: Perkin Elmer Series 200 solvent delivery system equipped with ABI 783A programable detector, Perkin Elmer ISS200 autosampler and PE Nelson 900 series data system, RP-18 reverse phase column (220×4.6 mm, Applied Biosystems Division), solvent A: 0.1M triethylammonium acetate, solvent B: $CH_3CN$, gradient: 8–20% B in 24 min, 20–40% B in 10 min, 40–8% B in 2 min, 8% B for 7 min, flow rate: 1 mL/min, detector: 260 nm.

The anion exchange HPLC system used to analyze the oligonucleotide products was as follows: Perkin Elmer Series 200 solvent delivery system equipped with ABI 783A programable detector, Perkin Elmer ISS200 autosampler and PE Nelson 900 series data system, Nucleopac PA-100 column (250×4 mm, Dionex Corporation); solvent A: 20 mM $LiClO_4$ and 20 mM NaOAc in $H_2O:CH_3CN$ (9:1, pH 6.5); solvent B: 600 mM $LiClO_4$ and 20 mM NaOAc in $H_2O:CH_3CN$ (9:1, pH 6.5); flow rate 1 mL/min; gradient: 0–60% B in 40 min; detector, 260 nm.

EXAMPLE 8

Enzymatic Analysis of Double Dye Labeled Oligonucleotides Prepared in Example 7

Enzymatic Digest with Snake Venom Phosphodiesterase and Alkaline Phosphatase: Snake venom phosphodiesterase (crotalus adamanteus) and alkaline phosphodiesterase (E. coli) were purchased from Pharmacia, Piscataway, N.J. Snake venom phosphodiesterase was obtained as powder which was dissolved in water at 1 mg/mL. A digest cocktail (55 gL) for each sample was prepared by mixing the following reagents: water (44 µL), 1 M $MgCl_2$ (0.8 µL), 0.5M Tris buffer, pH 7.5 (3.5 µL), alkaline phosphatase (4.0 µL) and snake venom phosphodiesterase (2.4 µL). Typically, 0.2 to 0.4 $A_{260}$ of oligoribonucleotide was dissolved in digest cocktail and heated at 37° C. for 8 h. After incubation, 3M sodium acetate (7 µL) and ethanol (155 µL) were added to each sample. Each sample was vortexed, cooled on dry ice for 10 min and then centrifuged for 10 min. The supernatants were carefully transferred to a set of new tubes and ethanol (452 µL) was added to each sample. The samples were vortexed and cooled on dry ice for 10 min and centrifuged for 10 min. The supernatants were carefully transferred to a set of new tubes. Samples were evaporated to dryness under vacuum. Each sample was dissolved in water (60 µL) and analyzed by reverse phase HPLC as described below.

Reverse-phase HPLC Analysis of Enzymatic Digests: The HPLC analyses were carried out on an Applied Biosystems 400 solvent delivery system equipped with ABI 783A programable detector, Perkin Elmer ISS200 autosampler and PE Nelson 900 series data system. Applied Biosystems RP-18 reverse phase column (220×4.6 mm) was used. The detector was set at 260 nm, 3% acetonitrile in 0.1M triethylammonium acetate was solvent A and 90% acetonitrile in water was solvent B. The gradient was 100% A for 5 min, 100–90% A in 30 min, 90–0% A in 30 min, 100% B for 5 min, 0–100% A in 2 min, 100% A for 15 min with flow rate 0.5 mL/min. The order of elution was dC, dG, T, dA, 6-carboxyfluorescein-(6-hydroxyhexylamide), thymidine-TAMRA linker conjugate. The enzymatic digestion study gave expected nucleoside composition and did not show any base modification.

Although only a few embodiments have been described in detail above, those having ordinary skill in the polynucleotide synthesis art will clearly understand that many modifications are possible in the preferred embodiment without departing from the teachings thereof. All such modifications are intended to be encompassed within the following claims.

---

We claim:

1. A synthesis support for the synthesis of 3'-labeled polynucleotides comprising a compound of the formula:

$$\begin{array}{c} TO-L_2 \\ \phantom{TO-}\diagdown \\ \phantom{TO-L_2}CR_3-L_1-NR_1R_2 \\ \phantom{TO-L_2CR}\diagup \\ \phantom{TO-L_2C}L_3 \\ \phantom{TO-L_2}\diagup \\ \phantom{TO-L_2}O \\ \phantom{TO-L_2}\diagdown \\ \phantom{TO-}C-CR_4R_5-O-CR_6R_7-C-NH-L_4-W \\ \phantom{TO-}\| \phantom{-CR_4R_5-O-CR_6R_7-}\| \\ \phantom{TO-}O \phantom{-CR_4R_5-O-CR_6R_7-}O \end{array}$$

where

T is an acid-cleavable hydroxyl protecting group;
$L_1$ is a linker for connecting a 3'-terminal nitrogen to carbon;
$L_2$ and $L_3$ are linkers for connecting oxygen and carbon;
W is a solid support;
$L_4$ is a linker for connecting the solid support to nitrogen;
$R_1$ and $R_2$ are nitrogen substituents individually selected from the group consisting of hydrogen, lower alkyl, nitrogen protecting group, or label; and
$R_3$ through $R_7$ are carbon substituents individually selected from the group consisting of hydrogen or lower alkyl.

2. The support of claim 1 wherein W is CPG.

3. The support of claim 2 wherein $L_4$ has the structure $$-(CH_2)_6-NH-\overset{O}{\underset{\|}{C}}-(CH_2)_2-\overset{O}{\underset{\|}{C}}-NH-(CH_2)_3-.$$

4. The support of claim 1 wherein W is nonswellable polystyrene.

5. The support of claim 4 wherein $L_4$ is methylene.

6. The support of claim 1 wherein T is 4,4'-dimethoxytrityl.

7. The support of claim 1 wherein $L_1$ has the structure $$-NH-\overset{O}{\underset{\|}{C}}-(CH_2)n-$$

where n ranges from 0 to 10.

8. The support of claim 7 wherein n ranges from 4 to 6.

9. The support of claim 1 wherein $L_2$ and $L_3$ are each methylene.

10. The support of claim 1 wherein $R_2$ is tetramethyl rhodamine.

11. The support of claim 1 wherein $L_3$ includes a disulfide bond.

12. A synthesis support for the synthesis of 3'-labeled polynucleotides comprising a compound of the formula:

$$\begin{array}{c} DMT-O-CH_2 \\ \phantom{DMT-O-}\diagdown \\ \phantom{DMT-O-CH_2}CH-(CH_2)_4-NH\text{-LABEL} \\ \phantom{DMT-O-CH_2C}\diagup \\ \phantom{DMT-O-CH_2}CH_2 \\ \phantom{DMT-O-C}\diagup \\ \phantom{DMT-O-C}O \\ \phantom{DMT-O-}\diagup \\ O=C \\ \phantom{O=}\diagdown \phantom{CH_2-O-CH_2-}O \\ \phantom{O=C}CH_2-O-CH_2-\overset{\|}{C}-NH-CH_2-W \end{array}$$

where DMT is 4,4'-dimethoxytrityl and W is non-swellable polystyrene.

13. A synthesis support for the synthesis of 3'-labeled polynucleotides comprising a compound of the formula:

$$\begin{array}{c} DMT-O-CH_2 \\ \diagdown \\ CH\mathord{+}CH_2)_4-NH\text{-LABEL} \\ \diagup \\ CH_2 \\ \diagup \\ O \\ \diagup \\ O=C \\ \diagdown \phantom{xx} O \phantom{xxx} O \phantom{xxx} O\\ CH_2-O-CH_2-\overset{\|}{C}-NH\mathord{+}CH_2)_6-NH-\overset{\|}{C}\mathord{+}CH_2)_2-\overset{\|}{C} \\ \phantom{xxxxxxxxxxxxxxxxxxxxxxxxxxxxxxxxxxx}| \\ \phantom{xxxxxxxxxxxxxxxxxxxxxxxxxxxxxxxxxxx}NH \\ \phantom{xxxxxxxxxxxxxxxxxxxxxxxxxxxxxxxxxxx}| \\ \phantom{xxxxxxxxxxxxxxxxxxxxxxxxxxxxxxxxxxx}(CH_2)_3 \\ \phantom{xxxxxxxxxxxxxxxxxxxxxxxxxxxxxxxxxxx}| \\ \phantom{xxxxxxxxxxxxxxxxxxxxxxxxxxxxxxxxxxx}W \end{array}$$

where DMT is 4,4'-dimethoxytrityl and W is CPG.

14. A synthesis support for the synthesis of 3'-labeled polynucleotides comprising a compound of the formula:

where DMT is 4,4'-dimethoxytrityl and W is non-swellable polystyrene.

15. A synthesis support for the synthesis of 3'-labeled polynucleotides comprising a compound of the formula:

where DMT is 4,4'-dimethoxytrityl and W is CPG.

16. A method for synthesizing 3'-labeled polynucleotides comprising the steps of:

(a) providing a synthesis support comprising a compound of the formula where,

T is an acid-cleavable hydroxyl protecting group;

$L_1$ is a linker for connecting a 3'-terminal nitrogen to carbon;

$L_2$ and $L_3$ are linkers for connecting oxygen and carbon;

W is a solid support;

$L_4$ is a linker for connecting the solid support to nitrogen;

$R_1$ and $R_2$ are nitrogen substituents individually selected from the group consisting of hydrogen, lower alkyl, nitrogen protecting group, or label; and $R_3$ through $R_7$ are carbon substituents individually selected from the group consisting of hydrogen or lower alkyl;

(b) treating the solid support with acid to remove the add-cleavable hydroxyl protecting group;

(c) adding a protected nucleoside monomer and a weak acid, forming a linkage;

(d) capping unreacted sites on the solid support;

(e) adding an oxidizing reagent;

(f) repeating steps (b)–(e) until the polynucleotide chain elongation is complete.

(g) cleaving the polynucleotide from the solid support; and (h) deprotecting the polynueleotide.

* * * * *